United States Patent [19]

Kleinberg

[11] Patent Number: 4,689,621
[45] Date of Patent: Aug. 25, 1987

[54] TEMPERATURE RESPONSIVE TRANSMITTER

[75] Inventor: Leonard L. Kleinberg, Annapolis, Md.

[73] Assignee: The United States of America as represented by the Administrator of the National Aeronautics and Space Administration, Washington, D.C.

[21] Appl. No.: 846,426

[22] Filed: Mar. 31, 1986

[51] Int. Cl.$^4$ .............................................. B08C 19/00
[52] U.S. Cl. ......................... 340/870.17; 340/870.16; 340/573; 128/736; 331/66
[58] Field of Search ...................... 340/870.16, 870.17, 340/573, 384 E; 128/631, 736, 903; 331/66, 116 R, 113 R; 309/310

[56] References Cited

U.S. PATENT DOCUMENTS

| | | | |
|---|---|---|---|
| 3,158,027 | 11/1964 | Kibler | 340/870.17 |
| 3,323,513 | 2/1965 | Gnadke | 128/631 |
| 3,534,728 | 10/1970 | Barrows | 340/870.17 |
| 3,739,279 | 6/1973 | Hollis | 128/631 |
| 4,107,625 | 8/1978 | Courier de Mere | 331/116 R |
| 4,177,800 | 12/1979 | Enger | 128/631 |
| 4,456,892 | 6/1984 | Vandergraaf | 331/66 |
| 4,560,959 | 12/1985 | Rokos et al. | 331/66 |
| 4,574,205 | 3/1986 | Nagano | 307/310 |

FOREIGN PATENT DOCUMENTS 0590844  1/1978  U.S.S.R. ........................ 331/116 R

OTHER PUBLICATIONS

J. R. Riley—"Crystal-Controlled, Surgically Implantable, Temperature Telemetry Transmitter"—Medical & Biological Engineering & Computing—May 1980, pp. 363-364.
Donaldson et al—"Silicone-Rubber Adhesive as Encapsulants for Microelectronic Implants; Effect of High Electric Fields and of Tensile Stress"—Medical & Biological Engineering & Computing-Nov. 1977—pp. 712-715.
Ramey et al—"A Temperature Monitoring System for Use on Normal Newborn Infants"—IEEE Trans. Instrum. & Meas. (U.S.A.), vol. 1M-21, No. 1 (Feb./1972).
Fenton—"Remote Temperature Measurements"—Instruments and Control Systems—vol. 43, No. 6—Jun. 1970.
Cupal et al—"A Pulsed Carrier Dual Channel; Biotelemetry System for Bouvine Nutrition Studies"—8th ISA Biomedical Sciences Instrumentation Symposium—May 1970—pp. 194-200.
Novinskii et al—"Quartz Thermometer with Oscillator Based on Field-Effect Transistors"—Instrum. & Exp. Tech. (U.S.A.), vol. 20, No. 3, pp. 2, 909-910, Dec. 1977.

Primary Examiner—John W. Caldwell, Sr.
Assistant Examiner—Mahmoud Fatahi-Yar
Attorney, Agent, or Firm—John O. Tresansky; John R. Manning; Harry Lupuloff

[57] ABSTRACT

A temperature responsive transmitter is provided in which frequency varies linearly with temperature. The transmitter includes two identically biased transistors connected in parallel. A capacitor, which reflects into the common bases to generate negative resistance effectively in parallel with the capacitor, is connected to the common emitters. A crystal is effectively in parallel with the capacitor and the negative resistance. Oscillations occur if the magnitude of the absolute value of the negative resistance is less than the positive resistive impedance of the capacitor and the inductance of the crystal. The crystal has a large linear temperature coefficient and a resonant frequency which is substantially less than the gain-bandwidth product of the transistors to ensure that the crystal primarily determines the frequency of oscillation. A high-Q tank circuit having an inductor and a capacitor is connected to the common collectors to increase the collector current flow which in turn enhances the radiation of the oscillator frequency by the inductor.

9 Claims, 2 Drawing Figures

4,689,621

TEMPERATURE RESPONSIVE TRANSMITTER

ORIGIN OF THE INVENTION

The invention described herein was made by an employee of the U.S. Government, and may be manufactured and used by or for the Government for governmental purposes without the payment of any royalties thereon or therefor.

TECHNICAL FIELD

The invention relates to temperature indicating devices, and more particularly to a transmitter in which frequency varies with temperature.

BACKGROUND ART

Accurate temperature measurement is essential to many fields. It is particularly important in the medical and veterinary fields, where internal temperature measurements indicate the health of a patient, or how the patient is reacting to various conditions. Measuring the internal temperature of a part of a patient's body may be accomplished by implanting, or ingesting, a temperature responsive transmitter.

Temperature responsive transmitters generally utilize a temperature sensitive component which varies in some physical characteristic, such as resistance, inductance, or capacitance, as temperature changes. This variation, in turn, is employed to change the frequency of the transmitter. Factors of interest which affect the design of a temperature responsive transmitter include linearity with temperature, frequency stability, frequency range, power consumption, output power, temperature range, accuracy, physical size, and cost.

Typical components which have been utilized in temperature responsive transmitters as temperature sensitive components to cause the frequency of the transmitter to change with temperature are thermistors, diodes, and piezoelectric crystals. Where a thermistor is used to vary the frequency of a transmitter, linearity and stability have proved to be unsatifactory. Where a diode is used, the voltage across the diode varies with temperature, and this voltage change must be converted to a change in frequency. To change the diode voltage to frequency requires complex circuitry, and the linearity of conversion is generally not satisfactory. The complex circuitry also increases the size of the transmitter which makes it more suitable for external use rather than internal use. When a piezoelectric crystal is used as the frequency determining element of a transmitter, linearity and frequency stability are satisfactory if the crystal is specially cut to have a large linear temperature coefficient. Previously, these specially cut crystals were relatively expensive, and this limited their use to situations in which the probability of loss of the temperature responsive transmitter was low.

SUMMARY OF THE INVENTION

Accordingly, it is an object of this invention to provide a temperature indicating transmitter.

It is a further object of this invention to provide a temperature responsive transmitter which is sufficiently small in size to be ingestible or implantable.

It is another object of this invention to provide a temperature responsive transmitter in which frequency varies linearly with temperature over a broad range of frequencies.

It is still another object of this invention to provide a temperature responsive transmitter in which frequency is stable over a broad range of frequencies.

It is still a further object of this invention to provide a temperature indicating transmitter which is accurate.

It is yet a further object of this invention to provide a temperature responsive transmitter with low power consumption and constant output power over its operating frequency range.

Yet a further object of this invention is to provide an oscillator circuit in which frequency varies linearly with temperature over a broad temperature range.

According to the present invention, these and other objects are attained by providing two identically biased transistors connected together in parallel. A capacitor is connected to the common emitters such that its capacitance is reflected to the common bases to generate negative resistance. The negative resistance and the capacitor are effectively in parallel, and oscillations will occur when an inductor, such as a crystal, is placed effectively in parallel with them and when the positive resistive impedance of the capacitor and the inductor is less than the negative resistance. The crystal is selected to have a linear temperature coefficient and a resonant frequency which is substantially less than the gain-bandwidth product of the transistors. A high-Q tank circuit having an inductor and a capacitor is connect to the common collectors.

DETAILED DESCRIPTION OF THE INVENTION

Figure 1:
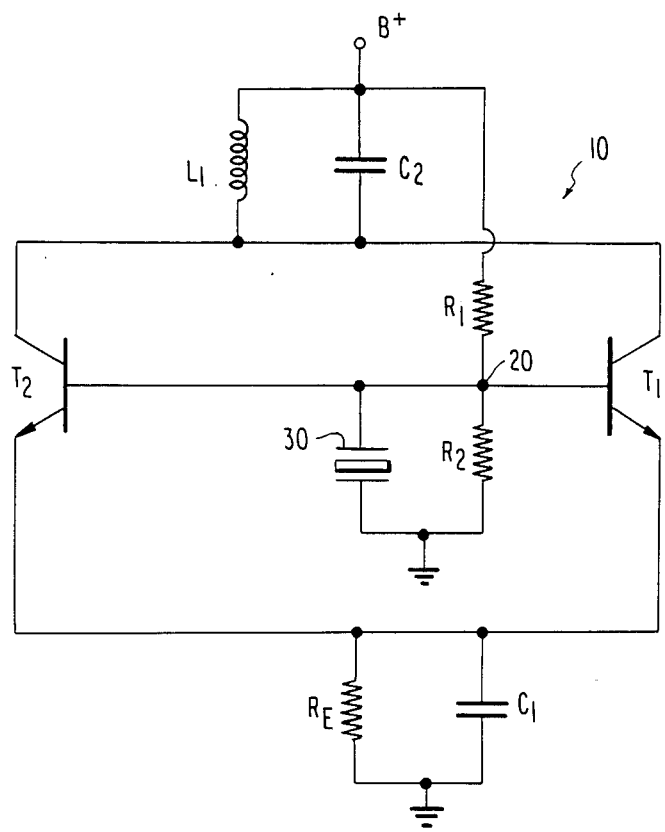
FIG. 1 is a schematic diagram of the temperature responsive transmitter of this invention.

Referring now to the drawings wherein like reference numerals and characters designate identical or corresponding parts throughout the several views, and more particularly to FIG. 1 wherein the temperature responsive transmitter 10 of the present invention is shown as including two transistors, $T_1$ and $T_2$, connected in parallel. Two transistors are advantageously used to double the output power of the transmitter 10 while simultaneously keeping the relationship between frequency and the gain-bandwidth product of the transmitter constant over its entire frequency range. To triple the output power of the transmitter 10, three transistors connected in parallel may be used. In the preferred embodiment of this invention, the two transistors may either be discrete or dual bipolar npn transistors, although other active devices may also be used. In the preferred embodiment, a pair of MAT-02 bipolar npn transistors manufactured by Precision Monolithics Incorporated of Santa Clara, Calif., have been found to perform satisfactorily.

The quiescent point of the transistors $T_1$ and $T_2$ is set by a voltage divider network connected between a source of B+ voltage and ground, and by a resistor $R_E$ connected between the common emitter electrodes and ground. The voltage divider network is formed of serially connected resistors $R_1$ and $R_2$ connected at their juncture 20 to the common base electrodes of the transistors thereby providing the bases with an intermediate voltage. In the preferred embodiment, the value of the B+ voltage is +3 volts, which may be supplied by a battery. Lithium batteries, which are very small in size and which are rated at 35 to 50 milliampere-hours to last at least 100 hours at a constant current drain of 0.1 milliampere, are preferred where the transmitter 10 is to be implanted or ingested in a patient for a prolonged period of time. Resistors $R_1$ and $R_2$ are both 1MΩ, which provides the bases with 1.5 volts at the juncture 20. Resistor $R_E$ is selected to be of a magnitude between 20 and 40 KΩ. A capacitor $C_1$ is connected in parallel with resistor $R_E$ so that resistor $R_E$ will affect only the direct current operation of the circuit. It also serves other purposes which will be discussed hereinafter. The value of $C_1$ in the preferred embodiment is 100 pf.

A piezoelectric crystal 30 is connected parallel with resistor $R_2$. The resonant frequency of the crystal 30 primarily determines the frequency of the transmitter 10. One factor that plays a part in determining the resonant frequency of the crystal 30 is its temperature coefficient. The temperature coefficient, in turn, depends upon the mechanical dimensions and the elastic constants of the crystal, and the mode of vibration involved. If a crystal which is specially designed and cut to have a large linear temperature coefficient is used, the frequency of the transmitter 10 will vary linearly with temperature over the linear temperature range of the crystal. In the preferred embodiment, a 262.144 kHz quartz crystal having a large positive linear temperature coefficient was employed. An example of such a crystal is quartz crystal TS-2, manufactured by Statek Corporation of Orange, Calif.

The piezoelectric crystal 30 may be represented by an equivalent circuit having a capacitance shunting a series resonant circuit. The capacitance is due to the crystal electrodes, and its value is very small, typically only a few picofarads. The series resonant circuit is comprised of an inductance, a capacitance, and a resistance. Typically, the value of the inductance is a few henries, the value of the capacitance is a few hundredths of a picofarad, and the value of the resistance is less than one hundred ohms. Crystal 30, therefore, is primarily an inductive impedance.

The inductive impedance of the crystal 30, along with the capacitance of the capacitor $C_1$, are effectively combined in parallel in the circuit of the transmitter 10 to create a two terminal oscillator. A two terminal oscillator can be defined as a negative resistance in parallel with a LC tank circuit. The inductive impedance of the crystal 30 provides the L required for the LC tank circuit. The capacitance of the capacitor $C_1$, which is reflected into the commonly connected bases, provides the capacitance required for the LC tank circuit. The negative resistance is provided by the action of the reflected capacitance from the capacitor $C_1$ on the circuit of the transmitter 10, and it is effectively in parallel with the LC tank circuit. Oscillations will occur in the two terminal oscillator if the magnitude of the absolute value of the negative resistance is less than the positive resistive impedance of the LC tank circuit. In terms of the embodiment of the invention illustrated, oscillations will take place if the magnitude of the absolute value of the negative resistance is larger than the positive resistance seen in the commonly connected bases of the transistors $T_1$ and $T_2$ due to the resistors $R_1$, $R_2$, and $R_E$. Also, in terms of the embodiment illustrated, the two terminals of the two terminal oscillator are the commonly connected bases and the commonly connected emitters of the transistors $T_1$ and $T_2$.

The value of the capacitance which is reflected into the joined bases of the transistors $T_1$ and $T_2$, and the value of the negative resistance generated by the capacitance of the capacitor $C_1$ are both functions of the value of the capacitor $C_1$, the gain-bandwidth product of the transmittor 10, and the frequency of the oscillation. The value of the reflected capacitance, $C_{ref}$, may be expressed as:

$$C_{ref} = \frac{C_1}{1 + \left(\frac{w_G}{w}\right)^2} \quad (1)$$

In equation (1), $w_G$ is the gain-bandwidth product of the transmitter 10, and w is the angular frequency of oscillation. The value of the negative resistance, $-R$, may be expressed as:

$$-R = \frac{1 + \left(\frac{w_G}{w}\right)^2}{w_G C_1} \quad (2)$$

In equations (1) and (2), the value of the gain-bandwidth product and the frequency of oscillation serve to limit the values of the reflected capacitance and the negative resistance. The gain-bandwidth product and the frequency of oscillation, which vary with each other in an inverse square relationship, also determine whether the crystal 30 primarily determines the frequency of oscillation. If the gain-bandwidth product is selected to be approximately four times the frequency of the crystal 30, then the crystal will primarily determine the frequency of oscillation. In the preferred embodiment, the gain-bandwidth product is 1 MHz, which is approximately four times the value of the 262.144 KHz crystal 30. Accordingly, the crystal 30 will primarily determine the frequency of oscillation.

The two terminal oscillator present in the circuit of the transmitter 10 is extremely stable. This is partly due to the way the circuit is biased. The resistors $R_1$ and $R_2$ are chosen so that the bias voltage at the commonly connected bases is equal to one half of the voltage of the source of B+ voltage to assure symmetry of the oscillator signal. This biasing arrangement, along with the circuit configuration of the transmitter 10, causes the gain of the circuit to be below the level at which hard limiting or clipping of the oscillator signal occurs. If the oscillator signal, which in the preferred embodiment is sinusoidal, is hard limited or clipped, then excessive noise is produced, which in turn, produces frequency instability. Furthermore, the low gain level, which prevents hard limiting or clipping, allows the transmitter 10 to operate at full power throughout each portion of each cycle.

The high stability of the two terminal oscillator present in the circuit of the transmitter 10 is also partly due to the capacitor $C_1$ and the reflected capacitance generated by the capacitor $C_1$. The voltage across the capacitor $C_1$, which controls the positive feedback, is approximately 180° out of phase with the voltage at the common bases of the transistors $T_1$ and $T_2$. The phase difference drives the common bases positive while simultaneously driving the common emitters negative in a regenerative process. This regenerative process is positive feedback, or equivalently, negative resistance. The difference between the voltage across the capacitor $C_1$ and the voltage at the common bases cancel, and this causes the quiescent point of the transistors $T_1$ and $T_2$ to remain constant. Frequently drift, which is caused by changes in the quiescant point, is substantially eliminated because the quiescant point remains constant. Accordingly, frequency stability is greatly enhanced.

The output from the two terminal oscillator is derived from the commonly connected collector electrodes. The current present in the common collector electrodes is multiplied by the Q of a parallel resonant LC network comprised of an inductor $L_1$, which functions as the radiating element for the transmitter 10, and a capacitor $C_2$. The Q of the LC network multiplies the current present in the common collectors to enhance the inductive current present in inductor $L_1$, which in turn increases the transmission distance. Inductor $L_1$ and capacitor $C_2$ are connected between the source of B+ voltage and the common collectors. In the preferred embodiment of this invention, the value of the inductor $L_1$ is 0.6 $\mu$h, and the vaue of the capacitor $C_2$ is 300 pf. The inductor $L_1$ may be wound in miniature size so as to be usable in an ingestible pill. For example, it may have 100 to 200 turns, a diameter of 3/16 of an inch, and a length of ½ of an inch.

Figure 2:
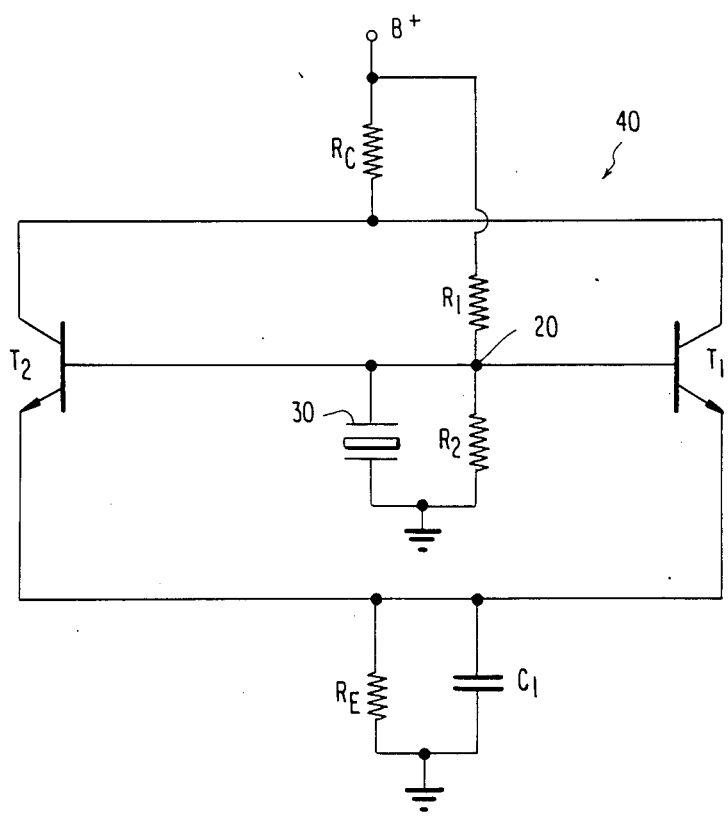
FIG. 2 is a schematic diagram of the temperature responsive oscillator of this invention.

In some applications it may be desirable to use the circuit of transmitter 10 as only an oscillator, and not as a transmitter. To accomplish this, the parallel LC network of FIG. 1 is replaced by a resistor $R_c$, as illustrated by the oscillator circuit 40 in FIG. 2. The preferred value of the resistor $R_c$ is 200Ω. The output from this circuit is preferably derived from resistor $R_c$ to maintain the symmetry of the circuit. The oscillatory frequency may also be determined by a frequency absorption meter or by a dip meter placed in close proximity to the oscillator.

Referring to FIG. 1, the temperature measuring transmitter 10 will produce a signal level of several microvolts in the antenna circuit of a receiver, not illustrated, positioned approximately a third of a meter away from the transmitter. Any receiver which can indicate the frequency of the transmitted signal can be used with the transmitter 10. The the transmitter 10 only generates a range of radio frequencies, which in the preferred embodiment is from 262.094 KHz to 262.194 KHz. The level of the signal produced by the transmitter 10 in the antenna circuit of the radio receiver will be the same throughout the frequency range of the transmitter 10. The transmitter 10 will have an approximate maximum transmission distance of one meter, but the most effective maximum transmission distance is approximately a third of a meter. To achieve these distances where the transmitter 10 is to be implanted or ingested in a patient, a frequency range is selected which will provide maximum transmissibility through living tissue, and which will not be subject to interference from other users of the radio frequency spectrum. The frequency range selected for the preferred embodiment which meets these requirements is centered on 262.144 KHz, which is the frequency of the quartz crystal 30.

The range of temperatures which may be measured by the temperature indicating transmitter 10 having the components identified herein is from $-10°$ C. or less to $+140°$ C. or more, with an accuracy of $0.01°$ C. Where the transmitter 10 is to be used to measure the internal temperature of a human body, the temperature range of interest is 30°–40° C., and an accuracy of 0.1° C. is required. With a temperature range of 30°–40° C., the frequency range of the preferred embodiment is 262.144 KHz±50 Hz, and the frequency stability 0.1 Hz. This translates to 9 Hz/° C., or 0.9 Hz/0.1° C., with an accuracy of at least 0.1° C.

Obviously, numerous modifications and variations of the present invention are possible in the light of this disclosure. It is therefore to be understood that within the scope of the appended claims the invention may be practiced otherwise than as specifically described therein.

I claim:

1. An ingestible size temperature responsive transmitter comprising:

a plurality of transistors having commonly directly connected base, collector, and emitter electrodes;

circuit means connected to said transistors and to a pair of terminals connectable to an unidirectional voltage source for identically biasing said transistors, said circuit means including a first resistance connected between said terminals and to said base electrodes at an intermediate point and a second resistance connected between one of said terminals and said emitter electrodes;

a first capacitor connected in parallel with said second resistance;

a crystal connected between said intermediate point and the one terminal, said crystal having a resonant frequency substantially one-fourth the gain-bandwidth product of said transistors to thereby establish the oscillatory frequency when the magnitude of the absolute value of the negative resistance generated by said first capacitor is less than the positive resistive impedance of the resonant circuit effectively formed by said crystal and said first capacitor; and a tank circuit composed of an inductance and a second capacitor connected between the other of said terminals and said collector electrodes.

2. The transmitter of claim 1 wherein said tank circuit has a high-Q to increase the collector current flow to thereby enhance the radiation of the oscillator frequency by said inductance.

3. The transmitter of claim 1 wherein said transistors are npn transistors.

4. The transmitter of claim 1 wherein said crystal has a large linear temperature coefficient.

5. The transmitter of claim 1 wherein the quiescent point of said transistors established by said circuit means is constant to thereby enhance frequency stability.

6. An ingestible size temperature responsive oscillator comprising:

a plurality of transistors having commonly directly connected base, collector, and emitter electrodes;

circuit means connected to said transistors and to a pair of terminals connectable to an unidirectional voltage source for identically biasing said transistors, said circuit means including a first resistance connected between said terminals and to said base electrodes at an intermediate point, a second resistance connected between one of said terminals and said emitter electrodes, and a third resistance connected between the other of said terminals and said collector electrodes;

a capacitor connected in parallel with said second resistance; and a crystal connected between said intermediate point and the one terminal, said crystal having a resonant frequency substantially one-fourth the gain-bandwidth product of said transistors to thereby establish the oscillatory frequency when the magnitude of the absolute value of the negative resistance generated by said capacitor is less than the positive resistive impedance of the resonant circuit effectively formed by said crystal and said capacitor.

7. The oscillator of claim 6 wherein the quiescent point of said transistors established by said circuit means is constant to thereby enhance frequency stability.

8. The oscillator of claim 6 wherein said transistors are npn transistors.

9. The oscillator of claim 6 wherein said crystal has a large linear temperature coefficient.

* * * * *